United States Patent [19]

Gilroy et al.

[11] Patent Number: 4,485,014

[45] Date of Patent: Nov. 27, 1984

[54] FILTER ASSEMBLY FOR CONNECTING INTERMEDIATE AN EPIDURAL CANNULA AND A SYRINGE

[75] Inventors: Keith Gilroy, San Marino, Calif.; Mark Johnson, Canterbury, England

[73] Assignee: Smiths Industries Public Limited Company, London, England

[21] Appl. No.: 445,630

[22] Filed: Nov. 30, 1982

[30] Foreign Application Priority Data

Dec. 8, 1981 [GB] United Kingdom ............ 8136958

[51] Int. Cl.³ ............................................. B01D 29/42
[52] U.S. Cl. .................................. 210/433.2; 210/445; 210/456; 210/927
[58] Field of Search ............ 210/237, 238, 248, 321.1, 210/323.3, 645, 445, 451, 500.2, 927, 433.2, 456, 446; 604/240, 241

[56] References Cited

U.S. PATENT DOCUMENTS

| | | | |
|---|---|---|---|
| 1,319,243 | 10/1919 | Powers | 604/241 |
| 2,855,927 | 10/1958 | Henderson | 604/241 |
| 3,803,810 | 4/1974 | Rosenberg | 55/159 |
| 3,834,124 | 9/1974 | Ichikawa | 210/198.1 |
| 3,905,905 | 9/1975 | O'Leary et al. | 210/436 |
| 4,009,714 | 3/1977 | Hammer | 210/445 |
| 4,009,715 | 3/1977 | Forberg et al. | 210/927 |
| 4,190,426 | 2/1980 | Ruschke | 210/927 |
| 4,240,424 | 12/1980 | Akhavi | 604/241 |

FOREIGN PATENT DOCUMENTS

| | | |
|---|---|---|
| WO80/00740 | 4/1980 | PCT Int'l Appl. |
| 363173 | 12/1931 | United Kingdom |
| 596201 | 12/1947 | United Kingdom |
| 1334555 | 10/1973 | United Kingdom |
| 1351325 | 4/1974 | United Kingdom |
| 1362117 | 7/1974 | United Kingdom |
| 1365815 | 9/1974 | United Kingdom |
| 1498249 | 3/1975 | United Kingdom |
| 1434013 | 4/1976 | United Kingdom |
| 1440027 | 6/1976 | United Kingdom |
| 2070708 | 9/1981 | United Kingdom |

*Primary Examiner*—Richard V. Fisher
*Assistant Examiner*—Wanda L. Millard
*Attorney, Agent, or Firm*—Pollock, Vande Sande & Priddy

[57] ABSTRACT

An epidural filter for connecting intermediate a syringe and an epidural cannula has a two-part housing formed with an inlet and an outlet. Within the housing a filter membrane is supported, parallel with the direction of fluid flow through the filter, by struts located on opposite sides of the membrane. Fluid is supplied to the filter from the syringe via a female Luer-tapered bore and distributed over the filter membrane along a channel and passages between the struts. The filter has an outlet coupling comprising a nose, having a bore, around which extends a screw-threaded collar. A clamping head is screwed into the collar about the nose so that the nose bears on a resilient bush contained within the head. The bush has a bore which receives the cannula so that when the clamping head is screwed onto the housing it forms a fluid-tight seal between the cannula and the housing.

6 Claims, 2 Drawing Figures

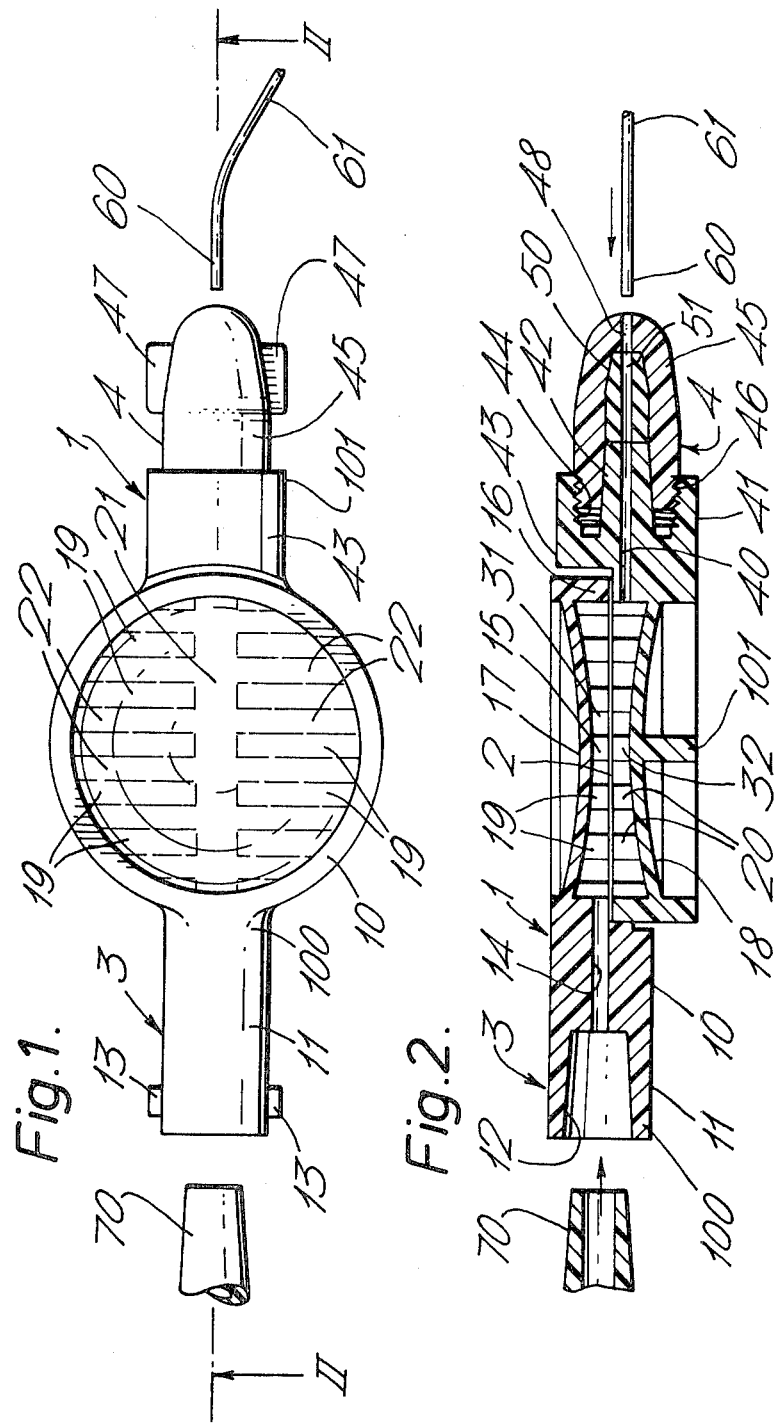

FILTER ASSEMBLY FOR CONNECTING INTERMEDIATE AN EPIDURAL CANNULA AND A SYRINGE

BACKGROUND OF THE INVENTION

This invention relates to filter assemblies.

The invention is more particularly concerned with filter assemblies that are adapted for connection to a fluid-flow line.

In many applications in medical practice, such as, in epidural anaesthesia, a filter assembly is connected in a fluid-flow line to trap unwanted material, bacteria, air bubbles and so on. The filter assembly may have a thin porous membrane or other filter element mounted in a housing intermediate its inlet and outlet.

The inlet and outlet of such previous filter assemblies are commonly both provided by Luer-tapered portions of the housing. The filter assembly is connected in a fluid-flow line by coupling the Luer portions to other suitable Luer fittings provided on the up-stream and down-stream fluid-flow lines. Such assemblies are satisfactory except for the fact that they can only be used with fluid-flow lines that are terminated by suitable coupling members. In practice, many fluid-flow lines are not provided with coupling members. It has, in the past therefore only been possible to use filter assemblies with such fluid-flow lines by providing special adaptors for coupling intermediate the filter assembly and the fluid-flow lines. Such adaptors present a disadvantage because they introduce additional possible sites for leakage, require additional time to assemble, and can increase the dead-space in the fluid lines. Any increase in the number of components required during surgery or anaesthesia is generally unwelcome.

BRIEF SUMMARY OF THE INVENTION

It is an object of the present invention to provide a filter assembly that can be used to avoid the above-mentioned disadvantages.

According to the present invention there is provided a filter assembly comprising a filter element mounted in a housing, said assembly being provided with first and second coupling means for connecting opposite sides of said filter element to respective tubular elements by which fluid can be supplied to and from the assembly, at least one of said coupling means including: a resilient member having a bore therethrough that is adapted to receive an end of a tubular element, said resilient member being mounted between the housing; and a clamping member that is operable to compress said resilient member about said tubular element so as to effect a fluid-tight seal between said tubular element and said housing.

The clamping member may be screw-threaded with the housing. The clamping member may have an aperture through which the tubular element extends into the resilient member. The housing may be formed with a nose portion that projects within the clamping member and bears on an end of said resilient bush. A collar may extend about said nose portion, said collar being formed with a screw thread on its inner surface that is arranged to engage a corresponding screw thread on said clamping member. The other coupling means may include a Luer-tapered portion. The filter element may be arranged substantially parallel to the direction of fluid-flow through said housing, said housing being provided with first and second support means for supporting opposite faces of said filter element. The first support means may define an elongate channel extending from an inlet to the assembly over a face of said filter element, and a plurality of passages extending from said channel towards the edge of said filter element. The housing may be a two part moulding, said first support means and said other coupling means being provided by one part, and said second support means and a part of said one coupling means being provided by said other part, said filter element being mounted between said two parts.

An epidural filter assembly according to the present invention will now be described, by way of example, with reference to the accompanying drawings.

BRIEF DESCRIPTION OF THE DRAWINGS

FIG. 1 is a plan view of the assembly; and

FIG. 2 is a sectional side elevation of the assembly along line II—II of FIG. 1.

DETAILED DESCRIPTION

The filter assembly comprises a housing 1 having a filter membrane 2 located between an inlet opening 3 and an outlet coupling 4.

The housing 1 has a rigid body 10 of transparent plastic material and substantially circular shape. The inlet opening 3 is provided at the rear end of the body 10 by a tubular extension 11 having a female Luer-tapered bore 12 and outwardly-extending locking lugs 13. The bore 12 opens through a smaller diameter passageway 14 into a circular filter chamber 15. The chamber 15 is defined by a cylindrical wall 16 and upper and lower domed faces 17 and 18 respectively, which present concave surfaces when viewed from the exterior of the assembly. Both faces 17 and 18 have vertical struts 19 and 20 respectively on their inner surfaces which extend parallel to one another transversely of the housing 1, from the edge to within a short distance of its center, thereby leaving a narrow channel 21. The channel 21 extends at right angles to the struts 19 and 20 longitudinally of the assembly, and communicates with side passages 22 that extend at right angles to the channel, to the edge of the membrane 2.

The struts 19 and 20 serve to support the filtering membrane 2 which has a 0.2 μm pore size. The membrane 2 is sandwiched between the two sets of struts 19 and 20, extending horizontally across the filtering chamber to divide it into upper and lower compartments 31 and 32 respectively.

The upper compartment 31 communicates with the inlet opening 3 whilst the lower compartment 32 communicates with the outlet coupling 4 via a bore 40.

The outlet coupling 4 is provided on a tubular forward extension 41 of the housing body 10. This extension comprises an inner male Luer-tapered nose 42 through which the bore 40 extends. An outer collar 43 coaxially encompasses the nose 42 and is provided, on its inner surface, with a screw thread 44. Surrounding the forward end of the nose 42 there is a hollow clamping head 45 that tapers towards its forward end. The outer surface at the rear of the clamping head 45 is formed with a screw thread 46 that engages the thread 44 on the inner surface of the collar 43. The forward, small-diameter, end of the head 45 has two radially-extending ears 47 by which the head can be gripped and rotated. An axial hole 48 extends through the tip of the head 45 and is aligned with the bore 40 in the nose 42.

Within the head 45 sits a resilient bush or gland 50 of rubber or plastics material. The bush 50 has an outer surface that conforms to the inner surface of the clamping head 45, that is, with a rear end of substantially cylindrical shape and a forward tapering end of substantially conical shape. The rear end of the bush 50 abuts the tip of the nose 42 and has an axial bore 51 therethrough which aligns, at one end with the bore 40 and, at the other end, with the hole 48 in the head 45. By screwing the head 45 onto the collar 43, the bush 50 is compressed between the nose 42 and the head, thereby constricting the bore 51 through the bush.

The body 10 of the housing 1 is formed in two parts 100 and 101. One part 100 comprises the inlet opening 3, the upper face 17 of the chamber 15 and the upper part of the wall 16. The other part 101 comprises the lower face 18, the lower part of the wall 16 and the outlet extension 41. These two parts are each integral mouldings. The assembly is constructed by placing the membrane 2 on the lower part 101 of the body 10 so that it is supported by the top of the lower part of the wall 16 and the struts 20, and then placing the upper part 100 of the body on top so that the upper surface of the membrane is contacted by the bottom of the top part of the wall and the struts 19. The membrane 2 and the two parts of the body are secured together by means of a suitable adhesive, solvent or by welding such as with radio frequency signals.

In operation, one end 60 of an epidural cannula 61 is pushed through the hole 48 in the head 45, and the bore 51 in the bush 50, and into the bore 40. The head 45 is grasped by the ears 47 and screwed further onto the collar 43 so as to compress the bush 50 about the cannula 61. The rear end of the bush 50 is contacted by the tip of the nose 42 thereby sealing the cannula with the bore 40.

A Luer-tapered male tubular member 70, such as, the tip of a syringe, is connected with the cannula 61 by insertion in the female Luer-tapered bore 12 at the rear end of the filter assembly. The syringe tip 70 is, in this way, connected to the upper filtering compartment 31, whilst the cannula 61 is connected to the lower filtering compartment 32. Fluid supplied from the syringe is distributed over the upper surface of the membrane 2 by the channel 21 and side passages 22. After passing through the membrane 2 the filtered fluid flows from the side passages 22 in the lower compartment to the central channel 21 and, from there, through the bore 40 to the cannula 61.

It can be seen that by arranging the filtering element substantially parallel to the direction of fluid-flow through the housing it is possible to provide a filter assembly of substantially flat configuration and relatively small internal volume.

The filter assembly also has the advantage that the cannula 61 can be directly connected to the filter assembly without the use of intermediate adaptors. This thereby reduces the risk of leakage and considerably facilitates connection to a syringe or other tubular member. It will be appreciated that the coupling 4 could be of various alternative forms where a resilient member is sealed about a tube. Also, the female Luer-tapered inlet on the assembly could be replaced by a coupling of the same form as the outlet coupling, or of any other form.

What we claim is:

1. A filter assembly for connecting intermediate an epidural cannula and a syringe and having a housing and a filter element mounted within said housing, said assembly including:
    first coupling means at one end of said assembly including a resilient member having a bore therethrough configured to receive an end of the epidural cannula,
    a clamping head having an aperture therein aligned with said bore through said resilient member,
    said clamping head defining therein a cavity for receiving said resilient member, said clamping head and said housing having cooperating screw threads for screwing said clamping head onto said housing to compress said resilient member between the housing and the clamping head about said cannula to effect a fluid-tight seal between said cannula and said housing;
    second coupling means at the opposite end of said housing,
    said second coupling means having a Luer-tapered portion adapted to receive said syringe,
    said first coupling means communicating with one side of said filter element and the second coupling means communicating with the other side of said filter element, said first and second coupling means being substantially aligned with one another.

2. A filter assembly according to claim 1, wherein said filter element extends transversely of the housing and substantially parallel to the direction of fluid-flow through said assembly.

3. A filter assembly according to claim 1, wherein said housing is provided with first and second support means located to support opposite faces of said filter element, said first support means defining an elongate channel extending from one of said coupling means over a face of said filter element, and a means defining a plurality of passages extending from said channel towards an edge of said filter element.

4. A filter assembly according to claim 3, wherein said housing is a two part moulding, said first support means and said second coupling means being provided by one part, and said second support means and a part of said first coupling means being provided by said other part, and wherein said filter element is mounted between said two parts.

5. A filter assembly according to claim 1, wherein said housing is formed with a nose portion, and wherein said nose portion projects within the clamping member and bears on an end of said resilient member.

6. A filter assembly according to claim 5, wherein said housing includes a collar extending about said nose portion, wherein said collar is formed with a screw thread on its inner surface, and wherein said clamping member is formed with a cooperating screw thread on its outer surface that engages the screw thread on said collar such that said clamping member can be screwed onto said housing to compress said resilient member.

* * * * *